(12) United States Patent
Archibald et al.

(10) Patent No.: US 11,312,674 B2
(45) Date of Patent: Apr. 26, 2022

(54) PROCESS FOR MAKING A FEED OF NORMAL BUTANOL, ISO-BUTANOL AND 2-ALKYL ALKANOL

(71) Applicant: Johnson Matthey Davy Technologies Limited, London (GB)

(72) Inventors: Fraser Archibald, London (GB); Adrian Lord, London (GB); Martin Smidt, London (GB); David Welch, London (GB)

(73) Assignee: Johnson Matthey Davy Technologies Limited, London (GB)

( * ) Notice: Subject to any disclaimer, the term of this patent is extended or adjusted under 35 U.S.C. 154(b) by 0 days.

(21) Appl. No.: 17/046,260

(22) PCT Filed: Apr. 11, 2019

(86) PCT No.: PCT/GB2019/051046
§ 371 (c)(1),
(2) Date: Oct. 8, 2020

(87) PCT Pub. No.: WO2019/197831
PCT Pub. Date: Oct. 17, 2019

(65) Prior Publication Data
US 2021/0078924 A1 Mar. 18, 2021

(30) Foreign Application Priority Data
Apr. 13, 2018 (GB) .................................. 1806127

(51) Int. Cl.
| | |
|---|---|
| *C07C 29/141* | (2006.01) |
| *B01D 3/14* | (2006.01) |
| *C07C 29/80* | (2006.01) |
| *C07C 31/12* | (2006.01) |
| *C07C 31/125* | (2006.01) |

(52) U.S. Cl.
CPC ............ *C07C 29/141* (2013.01); *B01D 3/146* (2013.01); *C07C 29/80* (2013.01); *C07C 31/12* (2013.01); *C07C 31/125* (2013.01)

(58) Field of Classification Search
CPC ....... C07C 29/141; C07C 29/80; C07C 31/12; C07C 31/125; B01D 3/146
See application file for complete search history.

(56) References Cited

U.S. PATENT DOCUMENTS

| 2,763,693 A | 10/1951 | Vander Woulde et al. |
| 3,119,876 A * | 1/1964 | Roming, Jr. ............ C07C 27/22 |
| | | 568/452 |

(Continued)

FOREIGN PATENT DOCUMENTS

| CN | 104961624 A | 10/2015 |
| CN | 105237350 A | 1/2016 |

(Continued)

*Primary Examiner* — Yate' K Cutliff
(74) *Attorney, Agent, or Firm* — BakerHostetler

(57) ABSTRACT

A process for the production of normal-butanol, iso-butanol and 2-alkyl alkanol is disclosed. The process comprises: hydrogenating a feed comprising normal butyraldehyde, iso-butyraldehyde and 2-alkyl alkenal to form a crude product stream comprising normal-butanol, iso-butanol, 2-alkyl alkanol, unreacted normal butyraldehyde, unreacted iso-butyraldehyde and one or more of unreacted 2-alkyl alkenal, 2-alkyl alkanal or 2-alkyl alkenol; separating the crude product stream to produce: a mixed butanol stream having higher concentrations of normal butanol, iso-butanol, unreacted normal butyraldehyde and unreacted iso-butyraldehyde than the crude product stream; and a crude 2-alkyl alkanol stream having higher concentrations of 2-alkyl alkanol and the one or more of unreacted 2-alkyl alkenal, 2-alkyl alkanal or 2-alkyl alkenol than the crude product stream; separating the mixed butanol stream to produce: a refined (Continued)

normal butanol stream having a higher concentration of normal butanol than the mixed butanol stream; and a crude iso-butanol stream having a higher concentration of iso-butanol than the mixed butanol stream; feeding the crude iso-butanol stream to a first polishing hydrogenation reactor wherein at least some of the unreacted iso-butyraldehyde is converted to iso-butanol to produce a polished iso-butanol stream; separating the polished iso-butanol stream to produce: a refined iso-butanol stream having a higher concentration of iso-butanol than the polished iso-butanol stream; and a light waste stream; separating the crude 2-alkyl alkanol stream to produce: an intermediate 2-alkyl alkanol stream having higher concentrations of 2-alkyl alkanol and the one or more of unreacted 2-alkyl alkenal, 2-alkyl alkanal or 2-alkyl alkenol than the crude 2-alkyl alkanol stream; and a heavy waste stream; feeding the intermediate 2-alkyl alkanol stream to a second polishing hydrogenation reactor wherein at least some of the one or more of unreacted 2-alkyl alkenal, 2-alkyl alkanal or 2-alkyl alkenol is converted to 2-alkyl alkanol to produce a polished 2-alkyl alkanol stream having a higher concentration of 2-alkyl alkanol than the intermediate 2-alkyl alkanol stream; separating the polished 2-alkyl alkanol stream to produce: a refined 2-alkyl alkanol stream having a higher concentration of 2-alkyl alkanol than the polished 2-alkyl alkanol stream; and an intermediate waste stream.

10 Claims, 6 Drawing Sheets

(56) References Cited

U.S. PATENT DOCUMENTS

2016/0075621 A1* 3/2016 Hashmi .................. B01J 25/02
560/99
2016/0257635 A1 9/2016 Eisenschmid et al.

FOREIGN PATENT DOCUMENTS

| CN | 105820037 A | 8/2016 |
| GB | 1362071 A | 7/1974 |
| GB | 1581898 A | 12/1980 |
| GB | 2560062 A | 8/2018 |
| WO | WO199812162 A1 | 3/1998 |
| WO | 2008056501 A1 | 5/2008 |
| WO | WO2012008717 A2 | 1/2012 |

* cited by examiner

PROCESS FOR MAKING A FEED OF NORMAL BUTANOL, ISO-BUTANOL AND 2-ALKYL ALKANOL

The present invention relates to a process for the production of normal-butanol, iso-butanol and 2-alkyl alkanol. More particularly it relates to the production of normal-butanol, iso-butanol and 2-alkyl alkanol by hydrogenating a feed comprising normal butyraldehyde, iso-butyraldehyde and 2 alkyl alkenal. Still more particularly, but not exclusively, it relates to the production of normal-butanol, iso-butanol and 2-ethyl hexanol by hydrogenating a feed comprising normal butyraldehyde, iso-butyraldehyde and 2 ethyl hexenal or the production of normal-butanol, iso-butanol and 2-propyl heptanol by hydrogenating a feed comprising normal butyraldehyde, iso-butyraldehyde and 2 propyl heptenal.

The production of 2-alkyl alkanol, such as 2-ethyl hexanol and 2-propyl heptanol takes place industrially on a large scale. The production can take place by aldol condensation and dehydration of aldehydes to produce 2-alkyl alkenals, followed by hydrogenation to the 2-alkyl alkanol. The hydrogenation typically proceeds via intermediate 2-alkyl alkanals or 2-alkyl alkenols. For example, normal butyraldehyde can undergo aldolization and dehydration to form 2-ethyl hexenal, which can be hydrogenated to 2-ethylhexanol. As another example, normal valeraldehyde can undergo aldolization and dehydration to form 2-propyl heptenal, which can be hydrogenated to 2-propyl-heptanol. Generally, the hydrogenation reaction does not go to completion and the crude product will contain the intermediates 2-alkyl alkanal and 2-alkyl alkenol and other side products such as aldehydes, ethers, esters and heavies resulting from multiples of the starting materials.

The production of normal-butanol and iso-butanol also takes place industrially on a large scale. The production can take place by hydrogenation of normal butyraldehyde and iso butyraldehyde.

The butyraldehyde or valeraldehyde used in the above process can be produced by hydroformylation of olefins, for example using the oxo process.

US2016075621 describes methods and systems for the simultaneous production of oxo-alcohols comprising n-butanol, isobutanol, and 2-ethylhexanol. The method comprises: providing a propylene stream and a syngas stream; hydroformylating the propylene stream and syngas stream to provide a first aldehyde stream comprising normal butyraldehyde and iso-butyraldehyde; aldolizing at least a portion of the normal butyraldehyde to provide a second aldehyde stream comprising 2-ethylhexenal; and hydrogenating simultaneously at least a portion of the first aldehyde stream and the second aldehyde stream to provide an alcohol stream comprising n-butanol, isobutanol, and 2-ethylhexanol; wherein the hydrogenating step is performed in a single hydrogenation reactor.

A single, combined hydrogenation step in the production of normal butanol, iso-butanol and 2-alkyl alkanol, such as described in US2016075621 may be desirable in that it may reduce the costs of the hydrogenation step. In particular, equipment costs may be reduced by a combined hydrogenation. However, such a combined hydrogenation step will only be commercially viable if the crude product stream resulting from the combined hydrogenation can be separated to produce on-spec product streams of the resulting normal-butanol, iso-butanol and 2-alkyl alkanol in an economical way. There is thus a need for efficient and effective refining schemes for separating normal-butanol, iso-butanol and 2-alkyl alkanol from the crude product stream. In addition to the desired normal-butanol, iso-butanol and 2-alkyl alkanol, the crude product stream will also contain side products and unreacted reactants from each of the different hydrogenations occurring within the combined hydrogenation step. One potential issue is the possibility of cross-contamination, where the side products of one reaction end up in the final product stream of the product of one of the other reactions. The refining of the crude product stream is therefore a particular problem requiring a specialist solution.

According to a first aspect of the present invention there is provided a process for the production of normal-butanol, iso-butanol and 2-alkyl alkanol the process comprising:

a. Hydrogenating a feed comprising normal butyraldehyde, iso-butyraldehyde and 2-alkyl alkenal to form a crude product stream comprising normal-butanol, iso-butanol, 2-alkyl alkanol, unreacted normal butyraldehyde, unreacted iso-butyraldehyde and one or more of unreacted 2-alkyl alkenal, 2-alkyl alkanal or 2-alkyl alkenol;

b. Separating the crude product stream to produce: a mixed butanol stream having higher concentrations of normal butanol, iso-butanol, unreacted normal butyraldehyde and unreacted iso-butyraldehyde than the crude product stream; and a crude 2-alkyl alkanol stream having higher concentrations of 2-alkyl alkanol and the one or more of unreacted 2-alkyl alkenal, 2-alkyl alkanal or 2-alkyl alkenol than the crude product stream;

c. Separating the mixed butanol stream to produce: a refined normal butanol stream having a higher concentration of normal butanol than the mixed butanol stream; and a crude iso-butanol stream comprising at least some of the unreacted iso-butyraldehyde and having a higher concentration of iso-butanol than the mixed butanol stream;

d. Feeding the crude iso-butanol stream to a first polishing hydrogenation reactor wherein at least some of the unreacted iso-butyraldehyde is converted to iso-butanol to produce a polished iso-butanol stream;

e. Separating the polished iso-butanol stream to produce: a refined iso-butanol stream having a higher concentration of iso-butanol than the polished iso-butanol stream; and a light waste stream;

f. Separating the crude 2-alkyl alkanol stream to produce: an intermediate 2-alkyl alkanol stream having higher concentrations of 2-alkyl alkanol and the one or more of unreacted 2-alkyl alkenal, 2-alkyl alkanal or 2-alkyl alkenol than the crude 2-alkyl alkanol stream; and a heavy waste stream;

g. Feeding the intermediate 2-alkyl alkanol stream to a second polishing hydrogenation reactor wherein at least some of the one or more of unreacted 2-alkyl alkenal, 2-alkyl alkanal or 2-alkyl alkenol is converted to 2-alkyl alkanol to produce a polished 2-alkyl alkanol stream comprising having a higher concentration of 2-alkyl alkanol than the intermediate 2-alkyl alkanol stream;

h. Separating the polished 2-alkyl alkanol stream to produce: a refined 2-alkyl alkanol stream a higher concentration of 2-alkyl alkanol than the polished 2-alkyl alkanol stream; and an intermediate waste stream.

The process according to the invention advantageously splits the separation into 2 parallel sets of separations. In each parallel set of separations, a polishing hydrogenation is included, which increases the yield of desired products while not creating cross contamination of the product streams. By carrying out the polishing hydrogenation after some separation steps have already occurred, the size of the polishing hydrogenation reactors may also be reduced. The polishing hydrogenation reactors have the further advantage that some slip of the unreacted normal butyraldehyde, unreacted iso-butyraldehyde and one or more of unreacted 2-alkyl alkenal, 2-alkyl alkanal or 2-alkyl alkenol can be tolerated in the hydrogenation in step (a), thus permitting the size of the hydrogenation equipment in step (a) to be kept economical.

The hydrogenation in step (a) may be operated under any suitable conditions. A catalyst will generally be used. Any suitable catalyst may be used. Generally, the active component of the catalyst will be based on metals from Groups VI to X. Suitable examples include copper, nickel, manganese, zinc, cobalt, palladium, ruthenium and iron. The catalyst may be supported. Any suitable support may be used. Suitable supports include alumina, silica or diatomaceous earth. A particularly suitable catalyst may be a supported copper chromite catalyst. The catalyst may also include a promoter to enhance selectivity. Any suitable promotor may be used. Barium may be a suitable promoter.

The hydrogenation may be carried out in the liquid or vapour phase. Any suitable configuration may be used and the reactor may be operated under any suitable conditions. Whilst the particular conditions selected will depend on the catalyst chosen, the hydrogenation may be carried out at a temperature of from about 60° C. to about 300° C., preferably from about 100° C. to about 200° C. and at a pressure of from 100 kPa to about 15 MPa.

Where a liquid phase hydrogenation is to be used, it may be performed in any suitable manner. In one arrangement, it may be carried out as downflow over packed beds of catalyst. A large recycle of cooled product may be mixed with the feed in order to remove the heat of reaction. One example of a suitable process is described in GB1362071 which is incorporated herein by reference. In an alternative arrangement one or more heat exchangers may be used to remove the heat of reaction.

Where a nickel catalyst is used in a liquid phase reaction, the temperature may be below about 150° C. at a pressure of from about 10 to about 30 bara. Where a copper chromite catalyst is used in a liquid phase reaction the temperature may be from about 100° C. to about 200° C. at a pressure of from about 15 to about 30 bara.

Where a gas phase hydrogenation is to be used, it may be performed in any suitable manner. A typical gas phase hydrogenation which may be used is that described in Hydrocarbon Processing, March 1983, pages 67 to 74, which is incorporated herein by reference.

Where a nickel catalyst is used in a gas phase reaction, the temperature may be from about 100° C. to about 150° C. at a pressure of from atmospheric to about 5 bara. Where a copper chromite catalyst is used in a gas phase reaction the temperature may be from about 135° C. to about 170° C. at a pressure of from atmospheric to about 5 bara. Where a promoted copper catalyst is used in a gas phase reaction the temperature may be from about 100° C. to about 250° C. at a pressure of from about 5 bara to about 30 bara. Where a copper zinc catalyst is used in a gas phase reaction the temperature may be from about 100° C. to about 270° C.

In this hydrogenation, the majority of the unsaturated aldehyde will be hydrogenated. The majority of the unsaturated 2-alkyl alkenal will be converted to the desired 2-alkyl alkanol. However, some products of partial hydrogenation will also be formed. Thus, one or both of 2-alkyl alkenol and 2-alkyl alkanal may be formed. Heavies, for example $C_{12}$, $C_{16}$, $C_{20}$ compounds when a $C_8$ alkyl alkenal is used and $C_{15}$, $C_{20}$, $C_{25}$ compounds when a $C_{10}$ alkyl alkenal is used, will also be generated during the hydrogenation. Pentanol may also be formed in the hydrogenation when the 2-alkyl alkanol being produced is 2-propyl heptanol, due to the hydrogenation or Cannizzaro type reaction of normal valeraldehyde which may be present as unreacted reactant from the production of 2-propyl heptenal from the aldolization of normal valeraldehyde.

Separating the crude product stream in step (b) preferably involves distillation, preferably in a crude product separation column. The crude product separation column is preferably operated to produce a light product in the top and a heavy product in the bottom. The crude product separation column is preferably operated such that any components heavier than normal butanol are preferentially contained in the heavy product, that is, in the crude 2-alkyl alkanol stream. The crude product separation column may thus be said to cut below normal butanol. Thus, the crude 2-alkyl alkanol stream preferably has higher concentrations of components heavier than normal butanol than the crude product stream.

Where the 2-alkyl alkanol being produced is 2-propyl heptanol the crude product separation column is preferably operated that any components lighter than pentanol are preferentially contained in the light product, that is, in the mixed butanol stream, and the crude product separation column may thus be said to be operated to cut between normal butanol and pentanol. Thus, the mixed butanol stream preferably has a higher concentration of components lighter than pentanol than the crude product stream. The cut between pentanol and normal butanol may be particularly advantageous when the 2-alkyl alkanol is 2-propyl heptanol, because of the presence of valeraldehyde in the hydrogenation in step (a) due to unreacted valeraldehyde from an upstream aldolization of normal valeraldehyde to produce the 2-propyl heptenal for the hydrogenation.

Where the 2-alkyl alkanol being produced is 2-ethyl hexanol the crude product separation column is preferably operated that any components lighter than iso-iso butyl butyrate are preferentially contained in the light product, that is, in the mixed butanol stream, and the crude product separation column may thus be said to be operated to cut between normal butanol and iso-iso butyl butyrate. Thus, the mixed butanol stream preferably has a higher concentration of components lighter than iso-iso butyl butyrate than the crude product stream.

Separating the mixed butanol stream in step (c) preferably involves distillation, preferably in a mixed butanol separation column. The crude iso-butanol stream is preferably taken as a side draw. Below the side draw the mixed butanol separation column preferably operates to separate iso-butanol and normal butanol, with the refined normal butanol stream preferably being taken at or near the bottom of the mixed butanol separation column. The refined normal butanol stream preferably contains a minimum fraction of iso-butanol such that it can meet the normal butanol specifications. Preferably the refined normal butanol stream contains at least 99.7 wt % normal butanol. Preferably the colour (APHA) of the refined normal butanol stream is not more than 5. Preferably the refined normal butanol stream contains not more than 0.1 wt % water. Preferably the refined normal butanol stream contains not more than 0.05 wt % aldehydes (typically as butyraldehydes). Preferably the acidity of the refined normal butanol stream is not more than 0.03 mg KOH/g. Preferably the sulphuric acid colour (APHA) of the refined normal butanol stream is not more than 20. Preferably the specific gravity 20° C./20° C. of the refined normal butanol stream is in the range of from 0.809 to 0.812. Preferably the distillation range (97% volume) of the refined normal butanol stream is 117-119° C. Preferably the refined normal butanol stream contains not more than 0.3 wt % and more preferably not more than 0.1 wt % iso-butanol. A refined normal butanol stream having such properties may be particularly commercially advantageous. The normal butanol content and iso-butanol content may be particularly important in producing a commercially advantageous refined normal butanol stream. The sulphuric acid colour (APHA) may also be an important parameter. Preferably the yield of normal butanol in the refined normal butanol stream is at least 95%, and more preferably at least 99%, compared to the crude product stream.

In a top section of the mixed butanol separation column, above the side draw, iso-butanol is preferably separated from the unreacted iso-butyraldehyde, unreacted normal butyraldehyde and water. Thus, separating the mixed butanol stream in step (c) preferably further comprises producing a butyraldehyde stream, having higher concentrations of the unreacted iso-butyraldehyde and the unreacted normal butyraldehyde than the mixed butanol stream. The butyraldehyde stream preferably has a higher concentration of water than the mixed butanol stream. The butyraldehyde stream is preferable recovered from at or near the top of the mixed butanol separation column. The unreacted iso-butyraldehyde and the unreacted normal butyraldehyde in the butyraldehyde stream typically have a normal to iso (n/i) ratio similar to that produced in an upstream oxo section for the hydroformylation of propylene. In general (depending on the conditions used in the oxo reaction), the n/i ratio varies between 1 and 30. It is desirable that the refined iso-butanol stream will contain only a very small fraction of normal butanol, for example less than 0.5 wt % normal butanol, and thus it is preferred that the unreacted normal butyraldehyde is largely separated from the crude iso-butanol. In that way, the unreacted normal butyraldehyde will not be hydrogenated in the first polishing hydrogenation reactor and ultimately cause contamination of the refined iso-butanol stream. The butyraldehyde stream is preferably decanted to remove a water rich phase, and subsequently recycled to the hydrogenation in step (a) or removed from the process. Any valeraldehydes in the mixed butanol stream, for example when the 2-alkyl alkanol being produced is 2-propyl heptanol, will boil very close to iso-butanol and are likely to accumulate in the crude iso-butanol stream. If sufficient water is present, water may be decanted from the crude iso-butanol stream. The mixed butanol separation column can, for example, be designed as a divided wall column or a conventional column. A divided wall column may be beneficial if the side draw is close to the feed tray.

Aldehydes, such as valeraldehyde and butyraldehyde, like many other unsaturated components, can contribute to the colour or sulphuric acid colour specification of an iso-butanol product. Low colour/sulphuric acid colour/aldehyde content are common specifications of an iso-butanol product and thus it is preferable to minimise the level of unsaturated components in the refined iso-butanol stream. To assist in achieving this, the crude iso-butanol stream is forwarded to the first polishing hydrogenation reactor, where unsaturated components are saturated with hydrogen. Any butyraldehyde that has not been separated in the previous step, for example, would be converted to butanol. Any valeraldehyde, for example, is converted to pentanol. It may be particularly desirable to carry out this step because it may be difficult to separate aldehydes, such as valeraldehyde for example, from the iso-butanol due to their close boiling points. There is typically a very low level of aldehyde specified for the refined iso-butanol stream. However, the total level of impurities specified for the refined iso-butanol stream is likely to be larger, and therefore a larger quantity of pentanol than valeraldehyde, or normal butanol than normal butyraldehyde, can be tolerated in the refined iso-butanol stream. Converting aldehydes to alkanols, such as valeraldehyde to pentanol or normal butyraldehyde to normal butanol, in the first polishing hydrogenation reactor may therefore be advantageous in achieving the desired specifications for the refined iso-butanol stream. As an example, in the case where valeraldehyde is present in the crude product stream, such as when the 2-alkyl alkanol being produced is 2-propyl heptanol, the main components in the polished iso-butanol stream are preferably iso-butanol, pentanol and a very small fraction of water.

The reactor, conditions and/or the catalyst used in the first polishing hydrogenation reactor may be the same or different to those used in the hydrogenation in step (a). However, generally the hydrogenation in the first polishing hydrogenation reactor will carried out in the liquid phase. This may be carried out over a packed bed of catalyst. The flow over the catalyst bed may be upflow or downflow. Any suitable catalyst may be used. In one arrangement, the active component of the catalyst may be nickel. Palladium or ruthenium may also be used as active components. The catalyst may be supported. Any suitable support may be used. Suitable supports include alumina, silica or diatomaceous earth. A promotor may be used. Generally, it will not be necessary to recycle cooled product to mix with the feed to order to remove the heat of reaction. The hydrogenation may be carried out at any suitable conditions. In one arrangement, the second hydrogenation may be carried out at a temperature of from about 80° C. to about 150° C. and at a pressure of from about 10 to about 35 bara.

Whilst a functioning flowsheet would be produced with the first polishing hydrogenation reactor upstream of the separation in step (c), it is advantageous for the first polishing hydrogenation reactor to be downstream of the separation in step (c) as in the present invention. If the first polishing hydrogenation reactor were upstream of step (c), pentanol resulting from the hydrogenation of valeraldehyde in the first polishing hydrogenation reactor would end up in the refined normal butanol stream. That could cause the refined normal butanol stream to be off specification. It is thus advantageous to position the first polishing hydrogenation reactor as in the present invention, so that the risk of pentanol ending up in the refined normal butanol stream is mitigated. Furthermore, by placing the first polishing hydrogenation reactor downstream of the step (c) separation, as in the present invention, the first polishing hydrogenation reactor does not have to be sized to handle the combined normal and iso-butanol flow in the mixed butanol stream. Instead, only the crude iso-butanol stream is fed to the first polishing hydrogenation reactor, which therefore handles a lower feed rate than would be the case if it were fed the mixed butanol stream and which can therefore be smaller and less expensive. The aldehyde concentration in the crude iso-butanol stream will also be higher than in the mixed butanol stream, because the mixed butanol stream is diluted by the normal butanol present and reaction rates will therefore be higher in the first polishing hydrogenation reactor when it is positioned after step (c). Thus, less catalyst and potentially a lower temperature can be used in the first polishing hydrogenation reactor, making its operation more cost effective.

The polished iso-butanol stream comprises iso-butanol. At least some of the unreacted normal butyraldehyde may be hydrogenated to normal butanol in the first polishing hydrogenation reactor. The polished iso-butanol stream may therefore comprise normal butanol.

Separating the polished iso-butanol stream preferably comprises feeding the polished iso-butanol stream to a polished iso-butanol separation column operated to produce on spec iso-butanol in the refined iso-butanol stream as a bottom stream, and the light waste stream in the top. The light waste stream is preferably a water rich stream. The light waste stream preferably comprises for example water and ether. The refined iso-butanol stream may have a higher concentration of normal butanol than the polished normal butanol stream. The refined iso-butanol stream preferably contains at least 99.5 wt % iso-butanol. The refined iso-butanol stream preferably contains not more than 0.5 wt % normal butanol. The sulphuric acid colour (APHA) of the refined iso-butanol stream is preferably not more than 20 and more preferably not more than 10. The refined iso-butanol stream preferably contains not more than 0.05 wt % water. The acidity of the refined iso-butanol stream is preferably not more than 0.03 mg KOH/g. The specific gravity 20° C./20° C. of the refined iso-butanol stream is preferably in the range of from 0.801 to 0.804. A refined iso-butanol stream having such properties may be particularly commercially advantageous. The iso-butanol content may be particularly important in producing a commercially advantageous refined iso-butanol stream.

The sulphuric acid colour (APHA) may also be an important parameter. Preferably the yield of iso-butanol in the refined iso-butanol stream is at least 95%, and more preferably at least 99%, compared to the crude product stream.

It may be that the crude product stream comprises valeraldehyde, which may be converted to pentanol in the first polishing hydrogenation reactor. This may particularly be the case where the 2-alkyl alkanol being produced is 2-propyl heptanol. Preferably the mass flow rate of valeraldehyde in the crude product stream is not more than 0.5% of the mass flow rate of isobutanol in the crude product stream. In that case, the level of pentanol in the refined iso-butanol stream may be sufficiently low that the refined iso-butanol stream remains on spec. It will be understood that the pentanol will generally be produced in the refined iso-butanol stream as opposed to the light waste stream due to the relative boiling points of iso-butanol and pentanol.

However, it may be that the level of valeraldehyde is such that the level of pentanol in the refined iso-butanol stream would be unacceptably high, or that there is a desire to otherwise recover the pentanol. Thus step (e) preferably comprises separating the polished iso-butanol stream to produce: a refined iso-butanol stream having higher concentrations of iso-butanol and normal butanol than the polished iso-butanol stream; a crude pentanol stream having a higher concentration of pentanol than the polished iso-butanol stream; and a light waste stream. Separating the polished iso-butanol stream preferably comprises feeding the polished iso-butanol stream to a polished iso-butanol separation column operated to produce on spec iso-butanol in the refined iso-butanol stream as a side draw, the crude pentanol stream in the bottoms, and the light waste stream in the top. The light waste stream is preferably a water rich stream. The light waste stream preferably comprises for example water and ether. Depending on the concentrations of water and pentanol the optimal position of the side draw can vary from top to bottom. The polished iso-butanol separation column may be designed as a divided wall column or a conventional column. A divided wall column may be beneficial if the side draw is close to the feed tray. In one embodiment, the polished iso-butanol separation column may be divided into two columns, with the crude pentanol stream being produced in the bottom of a first polished iso-butanol separation column and an overhead stream from the first polished iso-butanol separation column being passed to a second polished iso-butanol separation column in which the light waste stream is produced in the top and the refined iso-butanol stream is produced in the bottom. In another embodiment, the polished iso-butanol separation column may be divided into two columns, with the light waste stream being produced in the top of a first polished iso-butanol separation column and a bottom stream from the first polished iso-butanol separation column being passed to a second polished iso-butanol separation column in which the refined iso-butanol stream is produced in the top and the crude pentanol stream is produced in the bottom.

Alternatively, or additionally, if the refined iso-butanol stream contains an unacceptably high concentration of pentanol, the refined iso-butanol stream can be wholly or partly recycled to the separation of the crude product stream in step (b). As the separation in step (b) preferably cuts between pentanol and normal butanol, the excess pentanol can thus be removed. A purge stream of iso-butanol is preferably removed from the recycle to prevent an unacceptably high level of iso-butanol building up in the process.

Separating the crude 2-alkyl alkanol stream to produce: an intermediate 2-alkyl alkanol stream having higher concentrations of 2-alkyl alkanol and the one or more of unreacted 2-alkyl alkenal, 2-alkyl alkanal or 2-alkyl alkenol than the crude 2-alkyl alkanol stream; and a heavy waste stream may comprise any suitable means provided that it enables removal of the heavy waste stream. For example, the separation may be carried out by distillation in a first distillation zone. The distillation in the first distillation zone may be carried out by any suitable means. In one arrangement, it may be conducted using a crude 2-alkyl alkanol separation column, which may for example be a refluxed distillation column having from about 20 to about 50 theoretical stages. In one arrangement, the crude 2-alkyl alkanol separation column may include sieve or valve trays. In one another arrangement, a structured packing may be used. The distillation may be carried out at any suitable conditions. In one arrangement, the crude 2-alkyl alkanol separation column top pressure will be in the region of from about 0.05 bara to about 0.5 bara. The bottoms temperature will generally be kept below about 175° C. The heavy waste stream may comprise $C_{12}$, $C_{16}$ and $C_{20}$ compounds when the 2-alkyl alkanol is a $C_8$ 2-alkyl alkanol and $C_{15}$, $C_{20}$ and $C_{25}$ compounds when the 2-alkyl alkanol is a $C_{10}$ 2-alkyl alkanol.

The intermediate 2-alkyl alkanol stream is passed to the second polishing hydrogenation reactor wherein at least some of the one or more of unreacted 2-alkyl alkenal, 2-alkyl alkanal or 2-alkyl alkenol is converted to 2-alkyl alkanol to produce a polished 2-alkyl alkanol stream comprising 2-alkyl alkanol having a higher concentration of 2-alkyl alkanol than the intermediate 2-alkyl alkanol stream. As the majority of unsaturated aldehyde will preferably have been hydrogenated in the hydrogenation in steps (a) this second hydrogenation is preferably generally directed to completing any partial hydrogenation. Of course, where there is any unhydrogenated unsaturated aldehyde remaining in the feed to the second polishing hydrogenation reactor this will be subjected to hydrogenation. The reactor, conditions and/or the catalyst used in the second polishing hydrogenation reactor may be the same or different to those used in the hydrogenation of step (a). However, preferably the hydrogenation in the second polishing hydrogenation reactor is carried out in the liquid phase. This may be carried out over a packed bed of catalyst. The flow over the catalyst bed may be upflow or downflow. Any suitable catalyst may be used. In one arrangement, the active component of the catalyst may be nickel. Palladium or ruthenium may also be used as active components. The catalyst may be supported. Any suitable support may be used. Suitable supports include alumina, silica or diatomaceous earth. A promotor may be used. Generally, it will not be necessary to recycle cooled product to mix with the feed to order to remove the heat of reaction. The hydrogenation may be carried out at any suitable conditions. In one arrangement, the hydrogenation in the second polishing hydrogenation reactor may be carried out at a temperature of from about 80° C. to about 150° C. and at a pressure of from about 10 to about 35 bara.

Separating the polished 2-alkyl alkanol stream to produce: a refined 2-alkyl alkanol stream having a higher concentration of 2-alkyl alkanol than the polished 2-alkyl alkanol stream; and an intermediate waste stream may comprise any means provided that it enables removal of the intermediate waste stream. For example, the separation may be carried out by distillation carried out in a second distillation zone. The distillation in the second distillation zone may be carried out by any suitable means. The means may be the same or different to that used in the first distillation zone. In one arrangement, it may be conducted using a polished 2-alkyl alkanol separation column, which may for example be a refluxed distillation column having from about 20 to about 50 theoretical stages. In one arrangement, the polished 2-alkyl alkanol separation column may include sieve or valve trays. In one another arrangement, a structured packing may be used. The distillation may be carried out at any suitable conditions. In one arrangement, the polished 2-alkyl alkanol separation column top pressure will be in the region of from about 0.05 bara to about 0.5 bara. The bottoms temperature will generally be kept below about 175° C. The intermediate waste stream may comprise butyl butyrate for example. Where the 2-alkyl alkanol is 2-propyl heptanol, the intermediate waste stream preferably may for example comprise pentanol.

The refined 2-alkyl alkanol stream is preferably recovered from at or near the bottom of the second distillation zone. In one arrangement, the refined 2-alkyl alkanol stream will preferably have at least 98%, more preferably at least 99%, or yet more preferably at least 99.5% 2-alkyl alkanol. The colour (APHA) of the refined 2-alkyl alkanol stream is preferably not more than 5. The refined 2-alkyl alkanol stream preferably contains not more than 0.05 wt % water. The refined 2-alkyl alkanol stream preferably contains not more than 0.01 wt % aldehydes (typically as 2-alkyl alkanal). The refined 2-alkyl alkanol stream preferably contains not more than 0.01 wt % acidity (for example, as acetic acid in, for example, a refined 2-ethyl hexanol stream). Preferably the sulphuric acid colour (APHA) of the refined 2-alkyl alkanol stream is not more than 10. Preferably the specific gravity 20° C./20° C. of the refined 2-alkyl alkanol stream is in the range of from 0.831 to 0.834. Preferably the distillation range (97% volume) of the refined 2-alkyl alkanol stream is 183-186° C. A refined 2-alkyl alkanol stream having such properties may be particularly commercially advantageous. The 2-alkyl alkanol content may be particularly important in obtaining a commercially advantageous refined 2-alkyl alkanol stream. Preferably the yield of 2-alkyl alkanol in the refined 2-alkyl alkanol stream is at least 95%, more preferably at least 97% and yet more preferably at least 99%, compared to the crude product stream.

In accordance with a second aspect of the invention there is provided a process for the production of normal-butanol, iso-butanol and 2-alkyl alkanol the process comprising:

(a) Hydrogenating a feed comprising normal butyraldehyde, iso-butyraldehyde and 2-alkyl alkenal to form a crude product stream comprising normal-butanol, iso-butanol, 2-alkyl alkanol, unreacted normal butyraldehyde, unreacted iso-butyraldehyde and one or more of unreacted 2-alkyl alkenal, 2-alkyl alkanal or 2-alkyl alkenol;

(b) Separating the normal-butanol, iso-butanol, 2-alkyl alkanol in the crude product stream, wherein the separating comprises a first separation process in which the normal-butanol, the iso-butanol, the unreacted normal butyraldehyde and the unreacted iso-butyraldehyde are separated from the 2-alkyl alkanol and the one or more of unreacted 2-alkyl alkenal, 2-alkyl alkanal or 2-alkyl alkenol, a second separation process in which the normal butanol is separated from the iso-butanol and a third separation process in which the 2-alkyl alkanol is purified, wherein the second separation process and the third separation process are in parallel, and wherein the second separation process includes a step of hydrogenating at least some of the unreacted iso-butyraldehyde to iso-butanol, and wherein the third separation process includes a step of hydrogenating at least one of the one or more of unreacted 2-alkyl alkenal, 2-alkyl alkanal or 2-alkyl alkenol to 2-alkyl alkanol.

When the crude product steam comprises pentanol, the first separation preferably sends normal butanol to the second separation process and pentanol to the third separation process.

The separations may be carried out by any suitable means provided that it achieves the separation. Preferably the separation is carried out by distillation. Preferably the separations are carried out in columns. The distillation may be carried out by any suitable means. Preferably the distillation is carried out in a distillation column. For example, the distillation columns may be refluxed distillation columns. The distillation columns may have from about 20 to about 50 theoretical stages When the process is said to separate a first component from a second component it will be understood that most of the first component goes into a first stream and most of the second component goes in to a separate second stream. For example, at least 90 wt %, preferably at least 95 wt % and more preferably at least 99 wt % of the first component goes into the first stream and at least 90 wt %, preferably at least 95 wt % and more preferably at least 99 wt % of the second component goes in to the separate second stream.

Preferably the 2-alkyl alkenal is 2-ethyl hexenal, the 2-alkyl alkanol is 2-ethyl hexanol and the one or more of unreacted 2-alkyl alkenal, 2-alkyl alkanal or 2-alkyl alkenol is one or more of unreacted 2-ethyl hexenal, 2-ethyl hexanal or 2-ethyl hexenol. Preferably the 2-alkyl alkenal is 2-propyl heptenal, the 2-alkyl alkanol is 2-propyl heptanol and the one or more of unreacted 2-alkyl alkenal, 2-alkyl alkanal or 2-alkyl alkenol is one or more of unreacted 2-propyl heptenal, 2-propyl heptanal or 2-propyl heptenol. The process may be particularly advantageous for those separations, for example because a single plant may be built that is capable of carrying out either process. Thus, a plant may be built that can switch between the two processes in accordance with market conditions to maximise profit. There may be provided a process for operating a plant wherein the plant is operated according to a process of the invention in which the 2-alkyl alkenal is 2-ethyl hexenal, the 2-alkyl alkanol is 2-ethyl hexanol and the one or more of unreacted 2-alkyl alkenal, 2-alkyl alkanal or 2-alkyl alkenol is one or more of unreacted 2-ethyl hexenal, 2-ethyl hexanal or 2-ethyl hexenol for a first period of time and the plant is operated according to a process of the invention in which the 2-alkyl alkenal is 2-propyl heptenal, the 2-alkyl alkanol is 2-propyl heptanol and the one or more of unreacted 2-alkyl alkenal, 2-alkyl alkanal or 2-alkyl alkenol is one or more of unreacted 2-propyl heptenal, 2-propyl heptanal or 2-propyl heptenol for a second period of time. The first period of time may be before or after the second period of time.

Preferably the one or more of unreacted 2-alkyl alkenal, 2-alkyl alkanal or 2-alkyl alkenol is two or more of unreacted 2-alkyl alkenal, 2-alkyl alkanal or 2-alkyl alkenol. It may be that the one or more of unreacted 2-alkyl alkenal, 2-alkyl alkanal or 2-alkyl alkenol is unreacted 2-alkyl alkenal, 2-alkyl alkanal and 2-alkyl alkenol. More preferably the one or more of unreacted 2-alkyl alkenal, 2-alkyl alkanal or 2-alkyl alkenol is one or more or 2-alkyl alkanal or 2-alkyl alkenol. Most preferably the one or more of unreacted 2-alkyl alkenal, 2-alkyl alkanal or 2-alkyl alkenol is 2-alkyl alkanal and 2-alkyl alkenol. It will be appreciated that the hydrogenation in step (a) is likely to at least partially hydrogenate the 2-alkyl alkenal and so it is more likely that the partial hydrogenation products: 2-alkyl alkanal and 2-alkyl alkenol, are present in the crude product stream than the initial reactant: 2-alkyl alkenal.

One aspect of the invention may comprise any feature described in relation to another aspect of the invention. For example, the second aspect of the invention may comprise any feature described in relation to the first aspect of the invention and vice versa.

The feed comprising normal butyraldehyde, iso-butyraldehyde and 2-alkyl alkenal may be fed to the hydrogenation as a single stream or in multiple streams. The feed may be produced from an Oxo unit, with at least some of the product from the Oxo unit being sent to an aldolization unit to produce the 2-alkyl alkenal. Thus, the process may comprise reacting syngas with one or more alkenes to produce a mixture of aldehydes in an Oxo unit, passing at least some of the aldehydes to the hydrogenation and passing at least some of the aldehydes to an aldolization to produce 2-alkyl alkenal before passing the 2-alkyl alkenal to the hydrogenation. Preferably the alkenes comprise propene, the aldehydes are normal and iso-butyraldehyde and the 2-alkyl alkenal is 2-ethyl hexenal or the alkenes comprise propene and butene, the aldehydes are normal and iso butyraldehyde and valeraldehyde and the 2-alkyl alkenal is 2-propyl heptenal.

The present invention will now be described by way of example only with reference to the accompanying drawings in which.

Figure 4:
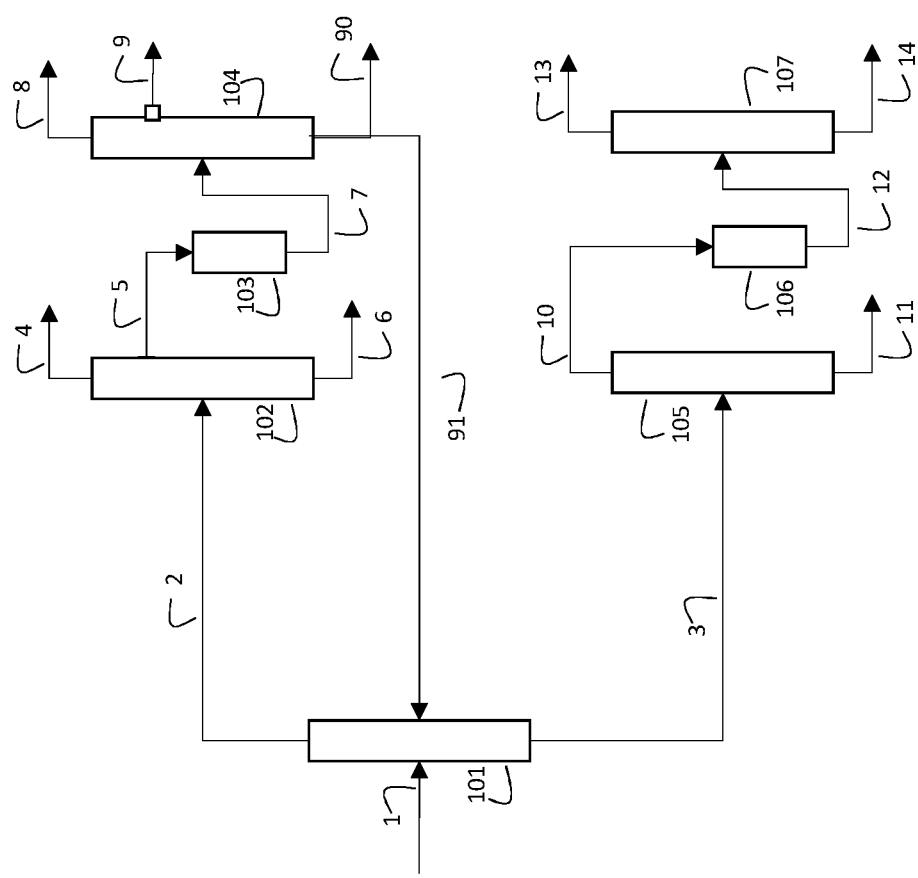
Figure 5:
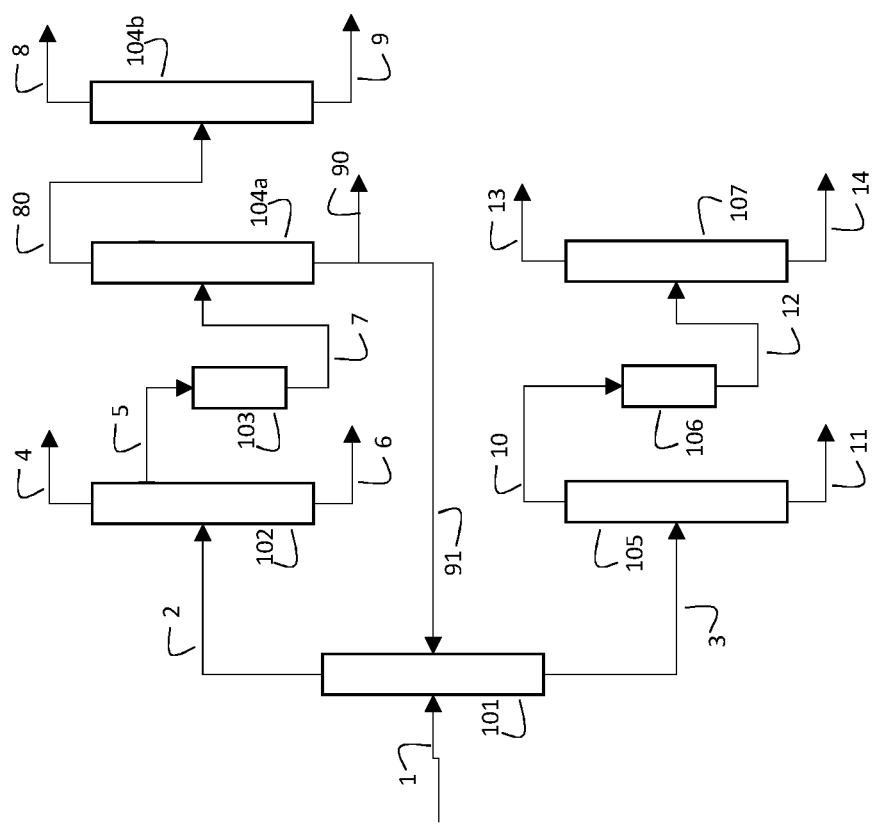
Figure 6:
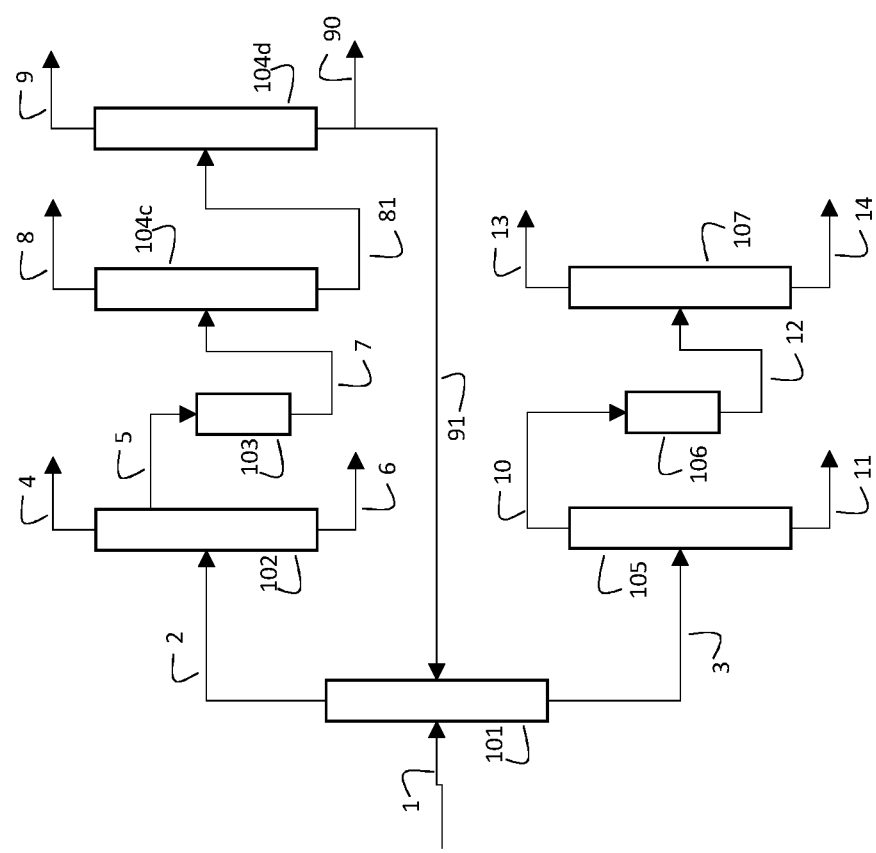

FIG. 4 is a schematic representation of a process according to the present invention; and FIG. 5 is a schematic representation of a process according to the present invention; and FIG. 6 is a schematic representation of a process according to the present invention It will be understood by those skilled in the art that the drawings are diagrammatic and that further items of equipment such as reflux drums, pumps, vacuum pumps, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

Figure 1:
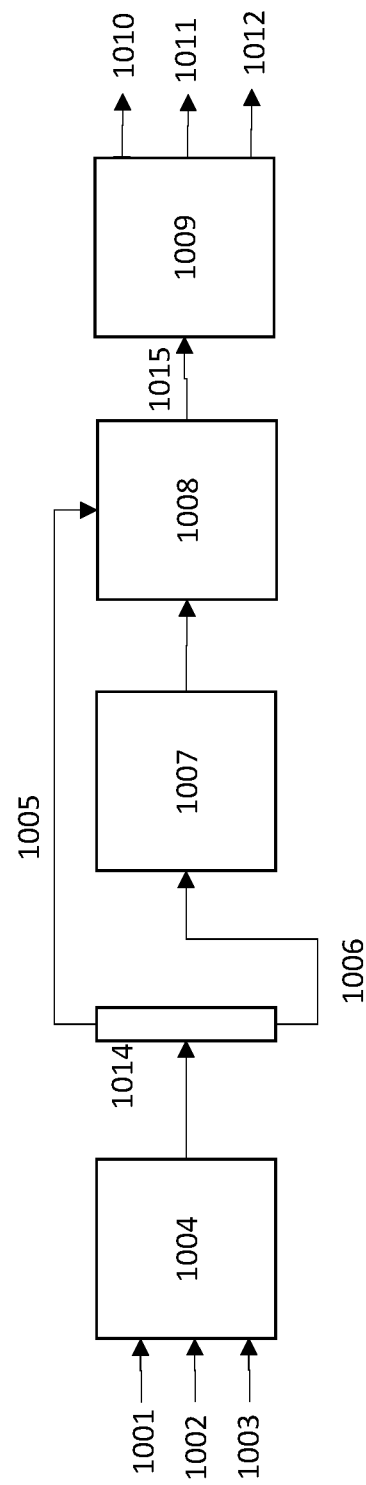
FIG. 1 is a block flow diagram of an overall process for the production of normal-butanol, iso-butanol and 2-propyl heptanol.

In FIG. 1, syngas 1001, propylene 1002 and butene 1003 are fed to an Oxo unit 1004. The product from the Oxo unit 1004 is separated in separator 1014 into a stream comprising normal and iso butyraldehyde 1005 and a stream comprising valeraldehyde 1006. The stream comprising valeraldehyde 1006 is fed to a aldolization unit 1007. In aldolization unit 1007, the valeraldehyde is aldolized to produce 2-propyl heptenal. The product of the aldolization unit 1007, which includes the 2-propyl heptenal, is fed to a hydrogenation reactor 1008. The stream comprising normal and iso butyraldehyde 1005 is fed directly to the hydrogenation reactor 1008. Thus, in hydrogenation reactor 1008 a feed comprising normal butyraldehyde, iso-butyraldehyde and 2-propyl heptenal is hydrogenated to form a crude product stream 1015 comprising normal-butanol, iso-butanol, 2-propyl heptanol, unreacted normal butyraldehyde, unreacted iso-butyraldehyde, unreacted 2-propyl heptenal, 2-propyl heptanal and 2-propyl heptenol. The product stream 1015 is fed to a separation 1009 to produce a refined iso-butanol stream 1010, a refined normal butanol stream 1011 and a refined 2-propyl heptanol stream 1012. The separation 1009 can, for example, be any of the separation schemes described below in relation to FIGS. 3-6.

Figure 2:
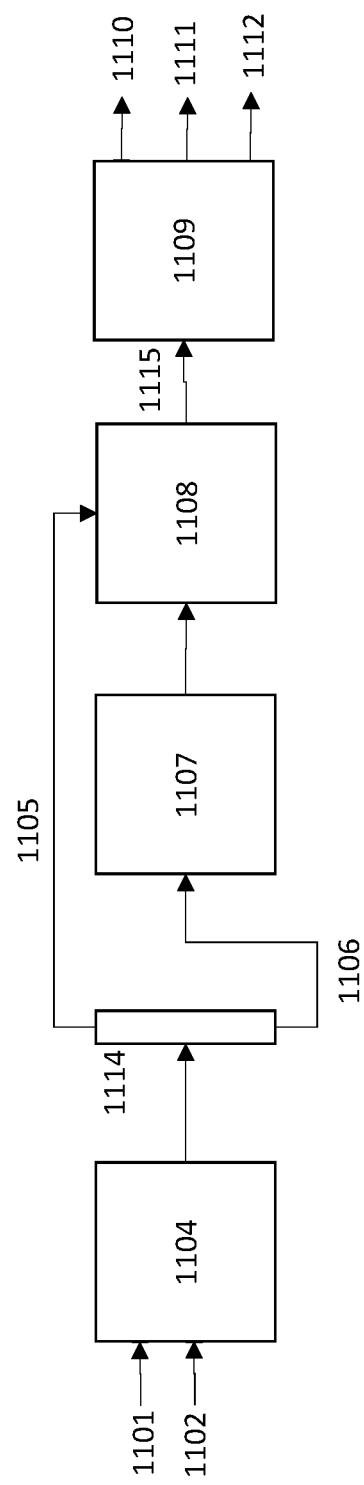
FIG. 2 is a block flow diagram of an overall process for the production of normal-butanol, iso-butanol and 2-ethyl hexanol.

In FIG. 2, syngas 1101 and propylene 1102 are fed to an Oxo unit 1104. The product from the Oxo unit 1104 is separated in separator 1114 into a stream comprising normal and iso butyraldehyde 1105 and a stream comprising normal butyraldehyde 1106. The stream comprising normal butyraldehyde 1106 is fed to a aldolization unit 1107. In aldolization unit 1107, the normal butyraldehyde is aldolized to produce 2-ethyl hexenal. The product of the aldolization unit 1107, which includes the 2-ethyl hexenal, is fed to a hydrogenation reactor 1108. The stream comprising normal and iso butyraldehyde 1105 is fed directly to the hydrogenation reactor 1108. Thus, in hydrogenation reactor 1108 a feed comprising normal butyraldehyde, iso-butyraldehyde and 2-ethyl hexenal is hydrogenated to form a crude product stream 1115 comprising normal-butanol, iso-butanol, 2-ethyl hexanol, unreacted normal butyraldehyde, unreacted iso-butyraldehyde, unreacted 2-ethyl hexenal, 2-ethyl hexanal and 2-ethyl hexenol. The product stream 1115 is fed to a separation 1109 to produce a refined iso-butanol stream 1110, a refined normal butanol stream 1111 and a refined 2-ethyl hexanol stream 1112. The separation 1109 can, for example, be any of the separation schemes described below in relation to FIGS. 3-6.

Figure 3:
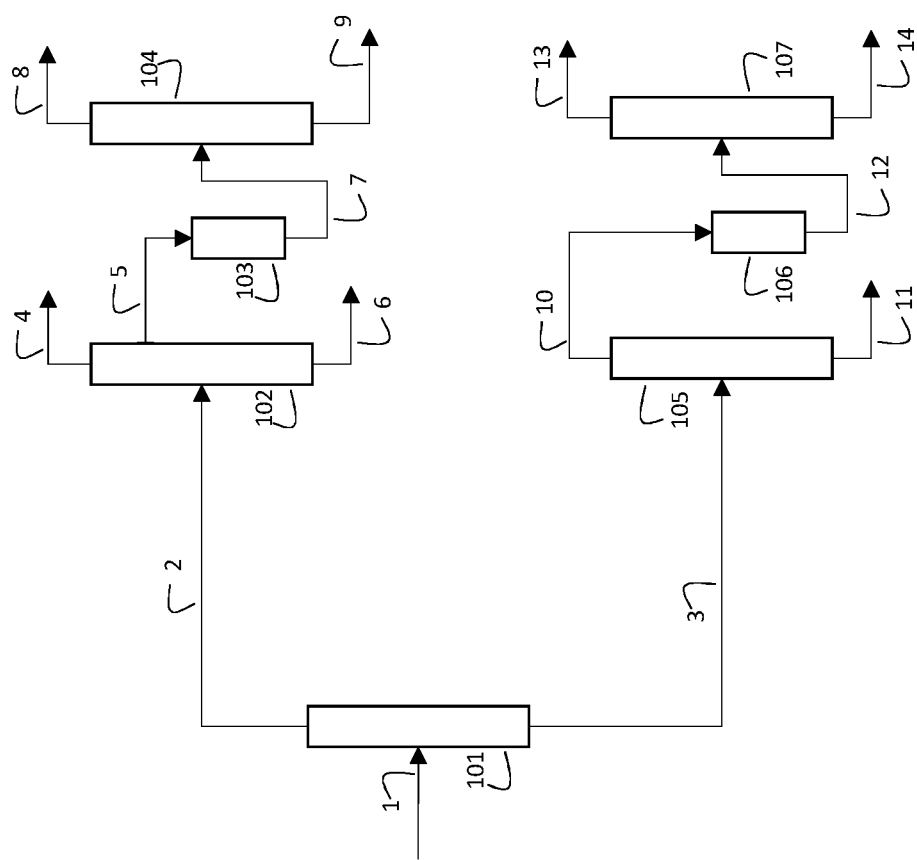
FIG. 3 is a schematic representation of a process according to the present invention.

In FIG. 3, a crude product stream 1 from a hydrogenation such as carried out in hydrogenation reactor 1008 or hydrogenation 1108 above is fed to a crude product separation column 101. The crude product separation column 101 is operated to cut between normal butanol, which goes overhead, and heavier components such as butyl butyrate or pentanol if present, which goes to the bottoms. A mixed butanol stream 2 is therefore produced from the top of the crude product separation column 101 and a crude 2-alkyl alkanol stream 3 is produced from the bottom of the crude product separation column 101.

The mixed butanol stream 2 is fed to a mixed butanol separation column 102, which operates to produce a butyraldehyde stream 4 from the top, a refined normal butanol stream 6 from the bottom and a crude iso-butanol stream 5 as a side draw. Unreacted aldehydes, such as butyraldehyde not removed in the butyraldehyde stream and, if present, valeraldehyde, from the hydrogenation will be in the crude iso-butanol stream 5. The crude iso-butanol stream 5 is fed to a first polishing reactor 103 in which the unreacted aldehydes are hydrogenated to the corresponding alkanols. A polished iso-butanol stream 7 leaves the first polishing reactor 103 and is fed to a polished iso-butanol separation column 104. A light waste stream 8 is produced from the top of the polished iso-butanol separation column 104 and a refined iso-butanol stream 9 is produced from the bottom.

The crude 2-alkyl alkanol stream 3 is fed to a first distillation zone, in the form of a crude 2-alkyl alkanol separation column 105, which is operated to remove any heavy components which may have been formed. These heavy components are removed in heavy waste stream 11, while an intermediate 2-alkyl alkanol stream 10 is removed from the top of the crude 2-alkyl alkanol separation column. The intermediate 2-alkyl alkanol stream 10 is then passed to the second polishing reactor 106. In this second polishing reactor 106 the intermediate 2-alkyl alkanol stream 10 is contacted with hydrogen. In general, this second polishing reactor 106 will enable unreacted 2-alkyl alkenal, 2-alkyl alkanal and 2-alkyl alkenol to be converted to the desired 2-alkyl alkanol thereby improving the purity of the product. For example, where the 2-alkyl alkanol is 2-ethyl hexanol, the second polishing reactor 106 will enable 2-ethyl hexenal, 2-ethyl hexenol and 2-ethyl hexanal to be converted to the desired 2-ethyl hexanol thereby improving the purity of the product. The polished 2-alkyl alkanol stream 12 leaving the second polishing reactor 106 is fed to a second distillation zone in the form of polished 2-alkyl alkanol separation column 107, where lights such as heptane or pentanol are separated and removed in intermediate waste stream 13 and the product 2-alkyl alkanol is recovered in refined 2-alkyl alkanol stream 14. In this embodiment, refined 2-alkyl alkanol stream 14 will preferably have an acid colour below 20 APHA, more preferably below 10 APHA.

In FIG. 4 a variation of the process in FIG. 3 is depicted. Like numerals in FIG. 4 refer to like items from FIG. 3 and are not described again. In FIG. 4, polished iso-butanol separation column 104 is operated to produce a crude pentanol stream 90 and recycle crude pentanol stream 91 from the bottom of polished iso-butanol separation column 104. The recycle crude pentanol stream 91 is fed back to the crude product separation column 101. Because the crude product separation column 101 in this embodiment is operated to cut between normal butanol and pentanol, the pentanol in recycle crude pentanol stream 91 will be separated into the crude 2-alkyl alkanol stream 3 by the crude product separation column 101. That may be advantageous where a high level of valeraldehyde is present in the crude product stream 1. The valeraldehyde in that stream will travel in the mixed butanol stream 2 and the crude iso-butanol stream 5 to the first polishing reactor 103, where it will react to form pentanol. In the process of FIG. 3, the pentanol would contaminate the refined iso-butanol stream 9, while as in the process of FIG. 4, the pentanol is separated in the polished iso-butanol column 104. Recycling the recycled crude pentanol stream 91 to the crude product separation column 101 takes advantage of the cut between normal butanol and pentanol in the crude product separation column 101 to send the pentanol into the crude 2-alkyl alkanol stream 3, from which it will be straightforwardly separated into the intermediate waste stream 13 in the polished 2-alkyl alkanol column 107, while any iso-butanol in the recycled crude pentanol stream 91 is sent to the mixed butanol stream 2 and hence can be recovered as product in the refined iso-butanol stream 9 from the polished iso-butanol separation column 104. Crude pentanol stream 90 acts as a purge to prevent components building open in the recycle loop.

In FIG. 5 a variation of the process in FIG. 4 is depicted. Like numerals in FIG. 5 refer to like items from FIGS. 3 and 4 and are not described again. In FIG. 5, the polished iso-butanol separation column 104 is split into two columns. In first polished iso-butanol separation column 104a, crude pentanol stream 90 and recycle crude pentanol stream 91 are produced in the bottom and a top stream 80 is passed to second polished iso-butanol separation column 104b from which refined iso-butanol stream 9 is produced at the bottom and light waste stream 8 is produced at the top.

In FIG. 6 a variation of the process in FIG. 4 is depicted. Like numerals in FIG. 6 refer to like items from FIGS. 3 and 4 and are not described again. In FIG. 6, the polished iso-butanol separation column 104 is split into two columns. In first polished iso-butanol separation column 104c, light waste stream 8 is produced from the top and a bottom stream 81 is passed to second polished iso-butanol separation column 104d from which refined iso-butanol stream 9 is produced at the top and crude pentanol stream 90 and recycle crude pentanol stream 91 are produced in the bottom.

The present invention will now be described with reference to the accompanying non-limiting examples.

EXAMPLE 1

A simulation of the process of FIG. 3 where the 2-alkyl alkenal is 2-ethyl hexenal and the 2-alkyl alkanol is 2-ethyl hexanol is performed using a crude product stream 1 containing considerably more by-products than would be expected in order to show that the proposed refining scheme would still be able to produce on spec products even under challenging conditions. A crude product stream 1 of 0.64 wt % water, 371 ppmw iso-butyraldehyde, 749 ppmw normal butyraldehyde, 14.4 wt % isobutanol, 23.0 w % normal butanol, 96 ppmw dibutylether, 136 ppmw IN-butylbutyrate, 856 ppmwt NN-butylbutyrate, 0.28 w % 2-ethyl hexanal, 59w % 2-ethyl hexanol, 1.25 wt % $C_{12}$ heavies and 1.16 wt % $C_{16}$ heavies, is sent to crude product separation column 101. Crude product separation column 101 is operated to cut in between n-butanol and IN-butylbutyrate.

The resulting mixed butanol stream 2 is sent to mixed butanol separation column 102. Mixed butanol separation column 102 is operated to produce a refined normal butanol stream 6 in the bottom with 0.1 wt % iso-butanol and 385 ppmw dibutylether, and, as a side draw, a crude isobutanol stream 5 containing 695 ppmw normal butanol. The butyraldehyde stream 4 produced as an overhead product of mixed butanol separation column 102 is condensed and cooled to 40° C. resulting in the liquid decanting into a water rich phase and an organic phase. The organic phase is used for the reflux and contains approximately 57.4 wt % aldehydes and 33.4 wt % iso-butanol and is saturated with water. The crude isobutanol stream 5 is fed to a first polishing reactor 103 where 99% of all aldehydes convert to the corresponding alkanol. The polished isobutanol stream 7 is then send to polished isobutanol separation column 104.

Polished isobutanol separation column 104 is operated to give 6.5 wt % water in the light waste stream 8 produced in the top. The refined isobutanol stream 9 contains <0.1 wt % normal butanol, about 20 ppm of dibutylether and another 20 ppm of water.

The crude 2-ethyl hexanol stream 3 produced in the bottom of crude product separation column 101 is fed to crude 2-ethyl hexanol separation column 105. Crude 2-ethyl hexanol separation column 105 is operated to give a temperature in the bottoms of 160° C., and a pressure of 0.2 bara, which yields a heavy waste stream 11 produced in the bottom of the crude 2-ethyl hexanol separation column 105 containing all $C_{12}$ and $C_{16}$ components fed to the crude 2-ethyl hexanol separation column 105. The heavy waste stream 11 thus contained 77 wt % $C_{12}$ and $C_{16}$ components, with the remainder being 2 ethyl-hexanol. The intermediate 2-ethyl hexanol stream 10 produced overhead is condensed and forwarded to the second polishing reactor 106 where 99% of all remaining unsaturated components are saturated. The polished 2-ethyl hexanol stream is forwarded to polished 2-ethyl hexanol separation column 107. Polished 2-ethyl hexanol separation column 113 is operated to give about 50 wt % 2-ethyl hexanol in the intermediate waste stream 13, produced as a top product from the polished 2-ethyl hexanol separation column 107, and 100 ppmw of NN-butylbutyrate in the refined 2-ethyl hexanol stream 14 produced as a bottom product from the polished 2-ethyl hexanol separation column 107. The respective yields for isobutanol, normal butanol and 2-ethyl hexanol are 97.5%, 99.7% and 99.0% with respect to the crude product stream fed to crude product separation column 101.

EXAMPLE 2

A simulation of the process of FIG. 6 where the 2-alkyl alkenal is 2-propyl heptenal and the 2-alkyl alkanol is 2-propyl heptanol is performed using a crude product stream 1 containing considerably more by-products than would be expected in order to show that the proposed refining scheme would still enable to produce on spec products even under challenging conditions. A crude product stream 1 of 0.33 wt % water, 330 ppmw iso-butyraldehyde, 667 ppmw normal butyraldehyde, 425 ppmw of normal valeraldehyde, 12.8 wt % iso-butanol, 20.0 wt % normal butanol, 0.86 wt % 2-methylbutanol, 1.45 wt % normal pentanol, 762 ppmw NN-butylbutyrate, 389 ppmw 2-ethyl hexanol, 60.7 wt % 2-propyl heptanol, 2.86 wt % 2-propyl heptenol, 796 ppmw $C_{12}$ heavies and 0.216 wt % $C_{20}$ heavies, is sent to crude product separation column 101. Crude product separation column 101 is operated to cut in between n-butanol and 2-methyl butanol.

The resulting mixed butanol stream 2 is sent to mixed butanol separation column 102. Mixed butanol separation column 102 is operated to produce a refined normal butanol stream 6 in the bottom with 100 ppmw iso-butanol, 13 ppmw of valeraldehyde and 17 ppmw of 2-methylbutanol, and, as a side draw, a crude isobutanol stream 5 containing 382 ppmw normal butanol. The butyraldehyde stream 4 produced as an overhead product of mixed butanol separation column 102 is condensed and cooled to 40° C. resulting in the liquid decanting into a water rich phase and an organic phase. The organic phase is used for the reflux and contains approximately 59 wt % $C_4$ aldehydes, 2.1 wt % $C_5$ aldehydes, 18.7 wt % water and 30.6 wt % iso-butanol. The crude iso-butanol stream 5 is fed to a first polishing reactor 103 where 99.9% of all aldehydes convert to the corresponding alkanol. The polished iso-butanol stream 7 is then send to first polished iso-butanol separation column 104c. First polished iso-butanol separation column 104c is operated to give 19 wt % water in the light waste stream 8. The bottom stream 81, still containing pentanols, is sent to second polished iso-butanol separation column 104d. Second polished isobutanol separation column 104d is operated to give a crude pentanol stream 90 in the bottom containing 50 wt % pentanols. In this example, the pentanols are not recycled. The refined iso-butanol stream obtained from the top of second polished isobutanol separation column 104d contains 33 ppmw of valeraldehyde, 5 ppmw of water and 415 ppmw of normal butanol.

The crude 2-propyl heptanol stream 3 produced in the bottom of crude product separation column 101 is fed to crude 2-propyl heptanol separation column 105. Crude 2-propyl heptanol separation column 105 is operated to give a temperature in the bottoms of 160° C., and a pressure of 85 mbara, which yields a heavy waste stream 11 produced in the bottom of the crude 2-propyl heptanol separation column 105 containing all $C_{12}$ and $C_{20}$ components fed to the crude 2-propyl heptanol separation column 105. The heavy waste stream 11 thus contained 66 wt % $C_{12}$ and $C_{20}$ components, with the remainder being 2-propyl heptanol. The intermediate 2-propyl heptanol stream 10 produced overhead is condensed and forwarded to the second polishing reactor 106 where 99% of all remaining unsaturated components are saturated. The polished 2-propyl heptanol stream 12 is forwarded to polished 2-propyl heptanol separation column 107. Polished 2-propyl heptanol separation column 107 is operated to give about 55 wt % 2-propyl heptanol in the intermediate waste stream 13, produced as a top product from the polished 2-propyl heptanol separation column 107, and less than 0.1 wt % 2-propyl heptenol in the refined 2-propyl heptanol stream 14 produced as a bottom product from the polished 2-propyl heptanol separation column 107. The respective yields for iso-butanol, normal butanol and 2-propyl heptanol are 95.4%, 99.3% and 95.0% with respect to the crude product stream 1 fed to crude product separation column 101.

It will be appreciated by persons skilled in the art that the above embodiments have been described by way of example only, and not in any limitative sense, and that various alterations and modifications are possible without departure from the scope of the invention as defined by the appended claims.

The invention claimed is:

1. A process for the production of normal butanol, iso-butanol and 2-alkyl alkanol the process comprising:
   (a) Hydrogenating a feed comprising normal butyraldehyde, iso-butyraldehyde and 2-alkyl alkenal to form a crude product stream comprising normal butanol, iso butanol, 2-alkyl alkanol, unreacted normal butyraldehyde, unreacted iso-butyraldehyde and one or more of unreacted 2-alkyl alkenal, 2-alkyl alkanal or 2-alkyl alkenol;
   (b) Separating the crude product stream to produce: a mixed butanol stream having higher concentrations of normal butanol, iso-butanol, unreacted normal butyraldehyde and unreacted iso-butyraldehyde than the crude product stream; and a crude 2-alkyl alkanol stream having higher concentrations of 2-alkyl alkanol and the one or more of unreacted 2-alkyl alkenal, 2-alkyl alkanal or 2-alkyl alkenol than the crude product stream;
   (c) Separating the mixed butanol stream to produce: a refined normal butanol stream having a higher concentration of normal butanol than the mixed butanol stream; and a crude iso-butanol stream comprising at least some of the unreacted iso-butyraldehyde and having a higher concentration of iso-butanol than the mixed butanol stream;

(d) Feeding the crude iso-butanol stream to a first polishing hydrogenation reactor wherein at least some of the unreacted iso-butyraldehyde is converted to iso-butanol to produce a polished iso-butanol stream;

(e) Separating the polished iso-butanol stream to produce: a refined iso-butanol stream having a higher concentration of iso-butanol than the polished iso-butanol stream; and a light waste stream;

(f) Separating the crude 2-alkyl alkanol stream to produce: an intermediate 2-alkyl alkanol stream having higher concentrations of 2-alkyl alkanol and the one or more of unreacted 2-alkyl alkenal, 2-alkyl alkanal or 2-alkyl alkenol than the crude 2-alkyl alkanol stream; and a heavy waste stream;

(g) Feeding the intermediate 2-alkyl alkanol stream to a second polishing hydrogenation reactor wherein at least some of the one or more of unreacted 2-alkyl alkenal, 2-alkyl alkanal or 2-alkyl alkenol is converted to 2-alkyl alkanol to produce a polished 2-alkyl alkanol stream having a higher concentration of 2-alkyl alkanol than the intermediate 2-alkyl alkanol stream; and (h) Separating the polished 2-alkyl alkanol stream to produce: a refined 2-alkyl alkanol stream having a higher concentration of 2-alkyl alkanol than the polished 2-alkyl alkanol stream; and an intermediate waste stream.

2. The process according to claim 1 wherein the one or more of unreacted 2-alkyl alkenal, 2-alkyl alkanal or 2-alkyl alkenol comprise 2-alkyl alkanal and 2-alkyl alkenol.

3. The process according to claim 1, wherein the separating the mixed butanol stream in (c) further comprises producing a butyraldehyde stream, having higher concentrations of the unreacted iso-butyraldehyde and the unreacted normal butyraldehyde than the mixed butanol stream.

4. The process according to claim 1, wherein the crude product stream comprises pentanol and step (e) comprises separating the polished iso-butanol stream to produce: a refined iso-butanol stream having a higher concentration of iso butanol than the polished iso-butanol stream; a crude pentanol stream having a higher concentration of pentanol than the polished iso-butanol stream; and a light waste stream.

5. A process for the production of normal butanol, iso-butanol and 2-alkyl alkanol the process comprising:

(a) Hydrogenating a feed comprising normal butyraldehyde, iso-butyraldehyde and 2-alkyl alkenal to form a crude product stream comprising normal butanol, iso butanol, 2-alkyl alkanol, unreacted normal butyraldehyde, unreacted iso-butyraldehyde and one or more of unreacted 2-alkyl alkenal, 2-alkyl alkanal or 2-alkyl alkenol; and, (b) Separating the normal butanol, iso-butanol, 2-alkyl alkanol in the crude product stream, wherein the separating comprises a first separation process in which the normal butanol, the iso-butanol, the unreacted normal butyraldehyde and the unreacted iso-butyraldehyde are separated from the 2-alkyl alkanol and the one or more of unreacted 2-alkyl alkenal, 2-alkyl alkanal or 2-alkyl alkenol, a second separation process in which the normal butanol is separated from the iso-butanol and a third separation process in which the 2-alkyl alkanol is purified, wherein the second separation process and the third separation process are in parallel, and wherein the second separation process includes a step of hydrogenating at least some of the unreacted iso-butyraldehyde to iso-butanol after the normal butanol is separated from the iso-butanol, and wherein the third separation process includes a step of hydrogenating at least one of the one or more of unreacted 2-alkyl alkenal, 2-alkyl alkanal or 2-alkyl alkenol to 2-alkyl alkanol.

6. The process according to claim 5, wherein the crude product steam comprises pentanol and the first separation sends normal butanol to the second separation process and pentanol to the third separation process.

7. The process according to claim 5, wherein the separations are carried out in columns.

8. The process according to claim 5, wherein the 2-alkyl alkenal is 2-ethyl hexenal, the 2-alkyl alkanol is 2-ethyl hexanol and the one or more of unreacted 2-alkyl alkenal, 2-alkyl alkanal or 2-alkyl alkenol is one or more of unreacted 2-ethyl hexenal, 2-ethyl hexanal or 2-ethyl hexenol.

9. The process according to claim 1, wherein the 2-alkyl alkenal is 2-propyl heptenal, the 2-alkyl alkanol is 2-propyl heptanol and the one or more of unreacted 2-alkyl alkenal, 2-alkyl alkanal or 2-alkyl alkenol is one or more of unreacted 2-propyl heptenal, 2-propyl heptanal or 2-propyl heptenol.

10. The process according to claim 5, wherein the 2-alkyl alkenal is 2-propyl heptenal, the 2-alkyl alkanol is 2-propyl heptanol and the one or more of unreacted 2-alkyl alkenal, 2-alkyl alkanal or 2-alkyl alkenol is one or more of unreacted 2-propyl heptenal, 2-propyl heptanal or 2-propyl heptenol.

* * * * *